(12) United States Patent
Schon

(10) Patent No.: US 6,682,519 B1
(45) Date of Patent: Jan. 27, 2004

(54) METHOD FOR INSERTING A MULTIPLE CATHETER ASSEMBLY

(75) Inventor: Donald A. Schon, Pheonix, AZ (US)

(73) Assignee: Medical Components, Inc., Harleysville, PA (US)

(*) Notice: Subject to any disclaimer, the term of this patent is extended or adjusted under 35 U.S.C. 154(b) by 0 days.

(21) Appl. No.: 09/585,150

(22) Filed: Jun. 1, 2000

(51) Int. Cl.⁷ .............................................. A61M 31/00
(52) U.S. Cl. ....................................... 604/508; 128/898
(58) Field of Search ...................... 604/43, 508, 500, 604/93.01, 264, 523, 27, 540, 541, 543, 19, 29, 39, 48, 173, 179–180, 905; 138/115, 117; 606/108

(56) References Cited

U.S. PATENT DOCUMENTS

| | | |
|---|---|---|
| 3,804,097 A | 4/1974 | Rudie |
| 3,823,720 A | 7/1974 | Tribble |
| 3,863,632 A | 2/1975 | Schwartz |
| 4,072,146 A | 2/1978 | Howes |
| 4,098,275 A | 7/1978 | Consalvo |
| 4,385,631 A | 5/1983 | Uthmann |
| 4,405,313 A | 9/1983 | Sisley et al. |
| 4,432,752 A | 2/1984 | Marlon |
| 4,451,252 A | 5/1984 | Martin |
| 4,493,696 A | 1/1985 | Uldall |
| 4,548,597 A | 10/1985 | Nelson |
| 4,583,968 A | 4/1986 | Mahurkar |
| 4,619,643 A | 10/1986 | Bai |
| 4,682,978 A | 7/1987 | Martin |
| 4,692,141 A | 9/1987 | Mahurkar |
| 4,770,652 A | 9/1988 | Mahurkar |
| 4,808,155 A | 2/1989 | Mahurkar |
| 4,895,561 A | 1/1990 | Mahurkar |
| 5,053,004 A | 10/1991 | Markel et al. |
| 5,053,023 A | 10/1991 | Martin |
| 5,057,075 A | 10/1991 | Moncrief et al. |
| 5,084,013 A | 1/1992 | Takase |
| 5,156,592 A | 10/1992 | Martin et al. |
| 5,197,951 A | 3/1993 | Mahurkar |
| 5,209,723 A | 5/1993 | Twardowski et al. |
| 5,336,220 A | 8/1994 | Ryan et al. |
| 5,374,245 A | 12/1994 | Mahurkar |
| 5,385,548 A | 1/1995 | Williams et al. |
| 5,480,380 A | 1/1996 | Martin |
| 5,624,413 A | * 4/1997 | Markel et al. ............... 604/523 |
| 5,718,692 A | * 2/1998 | Schon et al. ................ 604/264 |
| 5,776,111 A | 7/1998 | Tesio |
| 5,947,953 A | * 9/1999 | Ash et al. ................... 138/115 |

FOREIGN PATENT DOCUMENTS

| | | |
|---|---|---|
| CA | 1092927 | 1/1981 |

OTHER PUBLICATIONS

Hocken, A.G., "Percutaneous Femoral Vein Catheterization for Hemodialysis: A Single Needle Technique," *Clinical Nephrology*, vol. 12, No. 2, 1979, pp. 93–94.

Brochure entitled, "The MedComp TESIO Catheter", MED-COMP, Harleysville, PA, date unknown, 4 pages.

B. Canaud, J.J. Beraud, H. Joyeux, C. Moio. "Internal Jugular Vein Cannulation with Two Silicone Rubber Catheters" *Artificial Organs*, 1986; 10(5):397–403.

F. Tesio, et al., "Double Catheterization of the Internal Jugular Vein for Hemodialysis" *Artificial Organs*, 1994; 18(4):301–304.

* cited by examiner

*Primary Examiner*—LoAn H. Thanh
(74) *Attorney, Agent, or Firm*—Joseph E. Maenner; Monte & McGraw, P.C.

(57) ABSTRACT

A method for inserting a double catheter assembly into an area of a body to be catheterized is provided. A formula is included for determining the optimal size of dilator device to be used in the method provided.

19 Claims, 6 Drawing Sheets

METHOD FOR INSERTING A MULTIPLE CATHETER ASSEMBLY

BACKGROUND OF THE INVENTION

Catheters for the introduction or removal of fluids may be located in various venous locations and cavities throughout the body. Several types of catheters have been developed for fluid transduction applications including multiple lumen catheters, such as a dual lumen catheter in which one lumen introduces fluids and one lumen removes fluids, and multiple catheter assemblies, which comprise multiple, individual, typically single lumen catheters which are inserted through one or more incisions into an area to be catheterized. Examples of multiple catheter assemblies include the Tesio catheter and the SchonCath® catheter.

To insert any catheter into a blood vessel, it is generally necessary to identify the vessel by aspiration with a long hollow needle in accordance with the Seldinger technique. When blood enters a syringe attached to the needle, the syringe is disconnected and a thin guide wire is passed through the needle into the interior of the vessel. The needle is then removed, leaving the guide wire within the vessel. The guide wire projects beyond the surface of the skin.

Once the guide wire is placed within the vessel, a physician may choose to pass a catheter into the vessel directly over the guide wire, and remove the guide wire, leaving the catheter in position within the vessel. Alternatively, a dilator device can be passed over the guide wire to enlarge the hole. A catheter is then passed over the guide wire, and the guide wire and dilator are removed. Although employing a dilator is particularly useful when the catheter to be inserted is significantly larger in diameter than the guide wire, removing a dilator in the manner prescribed by most catheterization methods is associated with increased bleeding and the formation of blood clots at the insertion site.

Double catheter assemblies used for rapid withdrawal and/or infusion of blood and blood components or products and used repeatedly over weeks to months, are usually of a size equal to or larger than 12 French. They may be designed as two assemblies joined together through most of their length or as in the SchonCath® and Tesio double catheter systems designed as two independent catheters with lumens and inserted together either attached at some point or independent in which each lumen has a diameter of usually greater than 6 French. Such retained assemblies are preferably made of soft material to minimize trauma to the vessels during prolonged contact, and are therefore often difficult to insert without bending, kinking or crimping during insertion. When using these retained assemblies, a physician may find it is necessary to use an introducer sheath to facilitate insertion.

An introducer sheath is simply a large, stiff thin-walled tube which serves as a temporary conduit for the permanent catheter which is being placed. The introducer sheath is positioned by placing a dilator device inside of the introducer sheath and passing both the dilator and the introducer sheath together into the vessel. A guide wire, left in the vessel after insertion of the dilator-sheath assembly as described above, and the dilator(s) is (are) then removed, leaving the thin-walled introducer sheath in place. The dilator must be removed in order for the catheter to pass into and through the sheath. When the dilator is removed the sheath is left open with nothing to prevent blood from issuing out nor air from entering in. Thus significant blood loss can occur if there is any delay caused by difficulty in passing the catheter assembly into the sheath. An additional complication is that, with the dilator out, if the patient inspires deeply and creates negative pressure, air is sucked into the central vessels through the open sheath and results in air embolism. Air embolism is a potentially very serious complication and may be fatal.

In the case of a Tesio catheter assembly, an individual catheter, without a hub or an anchoring device, may be passed through the sheath and into the vessel. The sheath is then removed over the catheter. When a connecting means such as a retaining sleeve, or any type of anchoring device such as a Dacron® or other fabric anchoring cuff is permanently attached to the catheter, the sheath must be either larger than the cuff or comprise a tear-away portion which splits into two parts as the sheath is retracted. Even when no cuff is present and a tunneling procedure is commonly not performed, as with a Tesio assembly used for acute catheterization (U.S. Pat. No. 5,776,111), the assembly is so large and flexible that a sheath is often necessary to facilitation insertion. Once inserted, each of the proximal ends of the catheters in the assembly is stabilized, either by means of an anchoring device, subcutaneous tunneling as in chronic catheterization, or by affixing to the patient's skin as in acute catheterization.

Typical anchoring devices for such catheters and other venous and body cavity catheters and shunts involve use of a tissue ingrowth cuff, generally made of a fabric such as Dacron® or the like, fitted on a proximal portion of the catheter for stabilization of the catheter in a single position if the catheter is to be left in that position for a significant length of time. Surrounding tissue cells grow into the fabric stabilizing the catheter in that particular location. In using catheters having a fabric cuff, or other retaining devices or fittings, one stabilizing technique includes creating a subcutaneous tunnel, or similar opening, several centimeters caudal to the insertion site of the catheter for stabilization of the catheter using the cuff or other device. Subcutaneous tunnels and stabilizing devices are typically used, for example, for multi-lumen catheters and for catheter assemblies such as the Tesio and the SchonCath®.

In a typical tunneling procedure, the skin is anesthetized in a linear fashion for a distance of about 6–8 centimeters caudal to the insertion site. If tunneling is used for venous insertion, a second incision is made and a tunneling device such as a trocar is passed into the incision and out through the skin at the point of catheter insertion creating a subcutaneous tunnel. The catheter is attached to the tunneling device and pulled back through the skin tunnel.

For a self-retaining, double catheter assembly, such as a SchonCath®, in which the individual catheters are either permanently or adjustably linked in one location along their length by a retaining sleeve, subcutaneous anchoring is accomplished by positioning the retaining sleeve below the incision site and outside the area to be catheterized. The sleeve renders the assembly self-retaining such that the double tunneling procedure necessary to insert, for example, a Tesio catheter, is optional.

Both an adjustable catheter according to U.S. Pat. No. 5,718,692 and a Tesio catheter permit independent insertion and removal of the individual catheters such that dialysis need not be unnecessarily prolonged. Further, because the individual catheters in these assemblies can be adjusted within the vessel and in relation to one another, a physician is able to optimize catheter placement for a given location on a given patient. The ability to adjust individual catheters within a multiple catheter assembly represents a significant advantage over multiple lumen catheters, since positioning of catheters is particularly important to proper catheter functioning. For example, if the tip of a central venous catheter is not properly located within a vessel, the catheter may cause the condition of cardiac arrhythmia or otherwise inhibit blood flow. If the catheter tip is not properly located within a body cavity there may not be sufficient access to the tip to allow bodily fluid to properly flow through the catheter. Further, the catheter tip may damage a vessel wall and surrounding tissue if not properly placed within the vessel.

In addition to providing more desirable flow characteristics with less vessel damage than multiple lumen catheters, multiple catheter assemblies are generally formed of flexible catheter materials, and thus, provide more comfortable and efficient catheterization procedures than are possible with multiple lumen catheters. While beneficial for chronic catheterizations, multiple catheter assemblies are also useful for acute catheterizations, since these assemblies can be straightforwardly modified for convenient use during acute procedures (e.g. the Tesio assembly for acute procedures, U.S. Pat. No. 5,776,111), and can be inserted through a single incision as described in U.S. Pat. No. 5,624,413.

In view of the significant advantages offered by multiple catheter assemblies, there is significant interest in developing safer, more direct methods of inserting multiple catheter assemblies. Current single-incision insertion methods for double catheter assemblies require the use of dilator devices which, when removed during most catheterization procedures, can cause increased bleeding and clot formation at the insertion site and create an increased chance of forming an air embolism in the vessel. Thus, there is a need in the art for a simple method of inserting a double catheter assembly, such as a Schon catheter assembly, which requires only one procedure and which decreases the patient health risks associated with standard catheterization methods. The present invention fills this need.

BRIEF SUMMARY OF THE INVENTION

The present invention includes a method for inserting a multiple catheter assembly into an area of a body to be catheterized, the, assembly comprising a first and a second catheter, the method comprising the steps of (a): accessing an area to be catheterized and creating an access site, (b) inserting an introducer sheath into the area to be catheterized, (c) inserting a first guide wire and a second guide wire into the introducer sheath, (d) at least partially inserting a first dilator and a second dilator into the area to be catheterized, (e) removing the first dilator and the second dilator and blocking the flow of one or more of blood and air into and out of the area to be catheterized, (f) passing the distal portion of the first catheter over the first guide wire and passing the distal portion of the second catheter over the second guide wire, and (g) inserting each of the first and second catheters in juxtaposed relation into the area to be catheterized and blocking the flow of one or more of blood and air into and out of the area to be catheterized. In this embodiment, the area to be catheterized is a blood vessel, such as an internal jugular vein of a human. In this preferred embodiment, the vein is proximal to the right atrium of the heart of the human, and that the distal portion of the first catheter is closer to the heart than the distal portion of the second catheter.

In one embodiment of the invention, the multiple catheter assembly further comprises a retaining sleeve, and the method further comprises making an incision at the access site and creating a recessed area directly under the incision, which recessed area is sized to contain the retaining sleeve.

In another embodiment, the method further comprises attaching removable connectors, each including, for example, an extension tube having a clamp for controlling fluid flow through the connector, and each having fluid passageways therethrough to the proximal portions of the first and second catheters.

In yet other embodiments, each of the first dilator and the second dilator has a diameter of 11 French when measured in the transverse direction, and each of the two wires is from about 100 centimeters in length to about 120 centimeters in length.

In multiple embodiments, the incision made at the access site is from about 1 centimeter in length to about 1.5 centimeters in length, and the method further comprises closing the incision made at the access site. Optionally, the method comprises subcutaneously securing a proximal portion of the first catheter and a proximal portion of the second catheter by forming at least one subcutaneous tunnel and threading the proximal portion of at least one of the first and second catheters therethrough.

In a preferred embodiment, the sum of the diameters of the first and second dilators is at least 3 French greater than the sum of the diameters of the first and second catheters, and step (d) of the method described above further comprises maneuvering each of the first and second dilators vigorously and circumferentially within the area to be catheterized.

In various embodiments of the invention, the proximal portions of the first and second catheters each include at least one subcutaneous securement device. In other embodiments, the first catheter is longer than the second catheter, as measured longitudinally.

In another aspect, the invention includes a kit for performing an insertion of a multiple catheter assembly into a human, the kit comprising one or more components selected from the group consisting of a multiple catheter assembly comprising a first catheter and a second catheter, an introducer sheath, a dilator, a guide wire, and an instructional material, wherein the instructional material provides one or more of an outline, an illustration, and a description of a method for inserting a multiple catheter assembly into an area of a human to be catheterized, the method comprising the steps of:

(a) accessing an area to be catheterized and forming an access site, (b) inserting an introducer sheath into the area to be catheterized, (c) inserting a first guide wire and a second guide wire into the introducer sheath, (d) at least partially inserting a first dilator and a second dilator into the area to be catheterized, (e) removing the first dilator and the second dilator and blocking the flow of one or more of blood and air into and out of the area to be catheterized, (f) passing the distal portion of the first catheter over the first guide wire and passing the distal portion of the second catheter over the second guide wire, and (g) inserting each of the first and second catheters in juxtaposed relation into the area to be catheterized and blocking the flow of one or more of blood and air into and out of the area to be catheterized.

Optionally, a kit of the invention can further comprise one or more of a replacement catheter, a syringe, a tunneling device, a connector, and a clamp.

In another embodiment, the instructional material of a kit included in the invention provides one or more of an outline, an illustration, and a description of a method for inserting a multiple catheter assembly into an area of a human to be catheterized, the method further comprising the steps of making an incision at the access site and creating a recessed area directly under the incision, which recessed area is sized to contain the retaining sleeve, and at least partially inserting a first dilator and a second dilator into the area to be catheterized and maneuvering each of the first and second dilators vigorously and circumferentially within the area to be catheterized,

BRIEF DESCRIPTION OF THE SEVERAL VIEW OF THE DRAWINGS

The foregoing summary, as well as the following detailed description of preferred embodiments of the invention, will be better understood when read in conjunction with the appended drawings. For the purpose of illustrating the invention, there is shown in the drawings plural embodiments which are presently preferred. It should be understood, however, that the invention is not limited to the precise arrangements and instrumentality's shown. In the drawings, elements are not necessarily drawn to exact scale, and like numerals are used to indicate like elements throughout. In the drawings.

DETAILED DESCRIPTION OF THE INVENTION

Certain terminology is used in the following description for convenience only and is not limiting. The words "right," "left," "lower" and "upper" designate directions in the drawings to which reference is made. The words "proximal" and "distal" refer to directions away from and closer to, respectively, for example, the insertion ends of the first and second catheters in a double catheter assembly according to the present invention. The terminology includes the words above specifically mentioned, derivatives thereof, and words of similar import. The articles "a" and "an" are used herein to refer to one or to more than one (i.e. to at least one) of the grammatical object of the article. By way of example, "an introducer sheath" can refer to one introducer sheath or to more than one introducer sheath, unless specifically stated otherwise.

Figure 2:
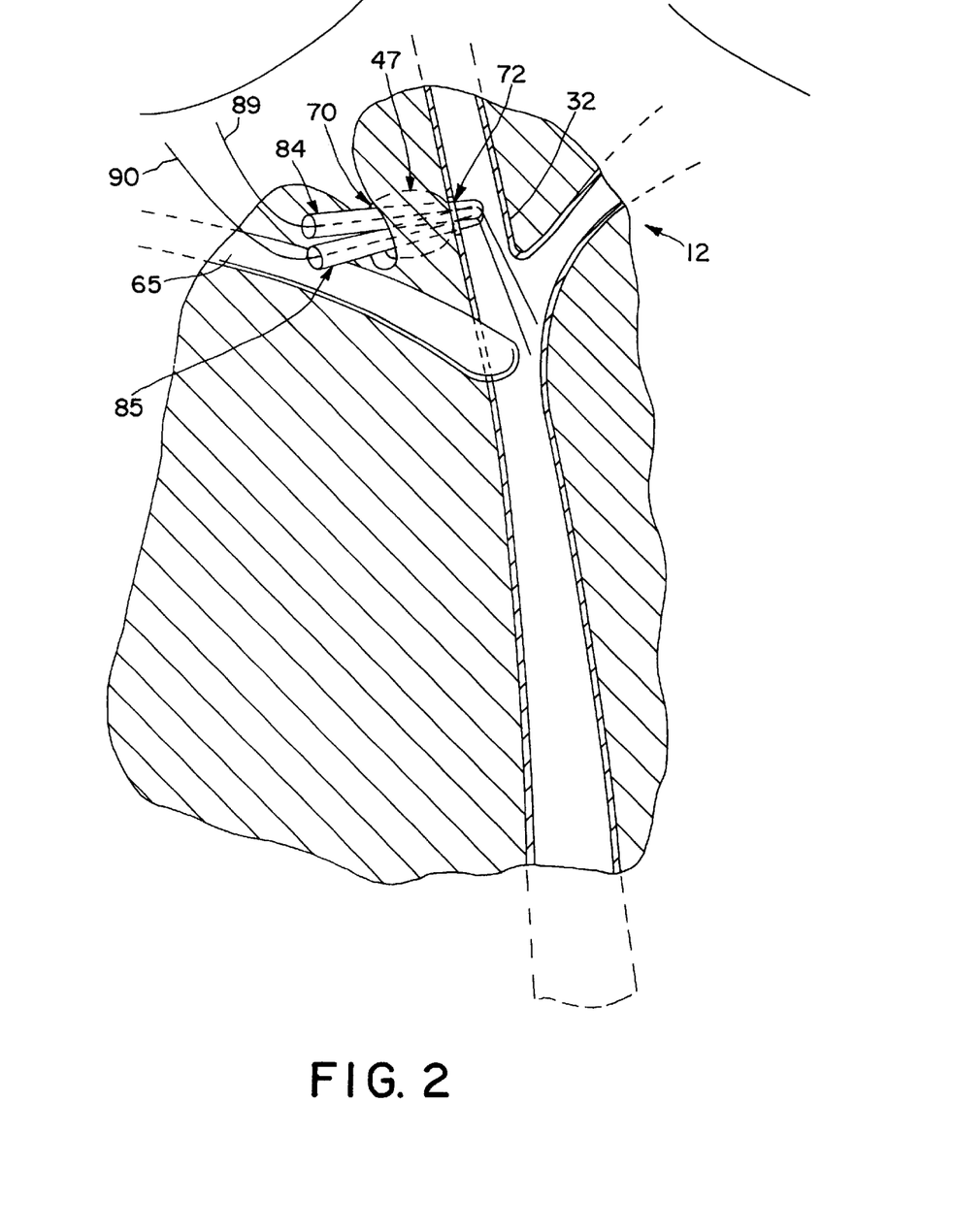
FIG. 2 is a partially broken-away diagrammatic view of a first dilator and a second dilator positioned within the internal jugular vein, after formation of the recessed area.
Figure 3:
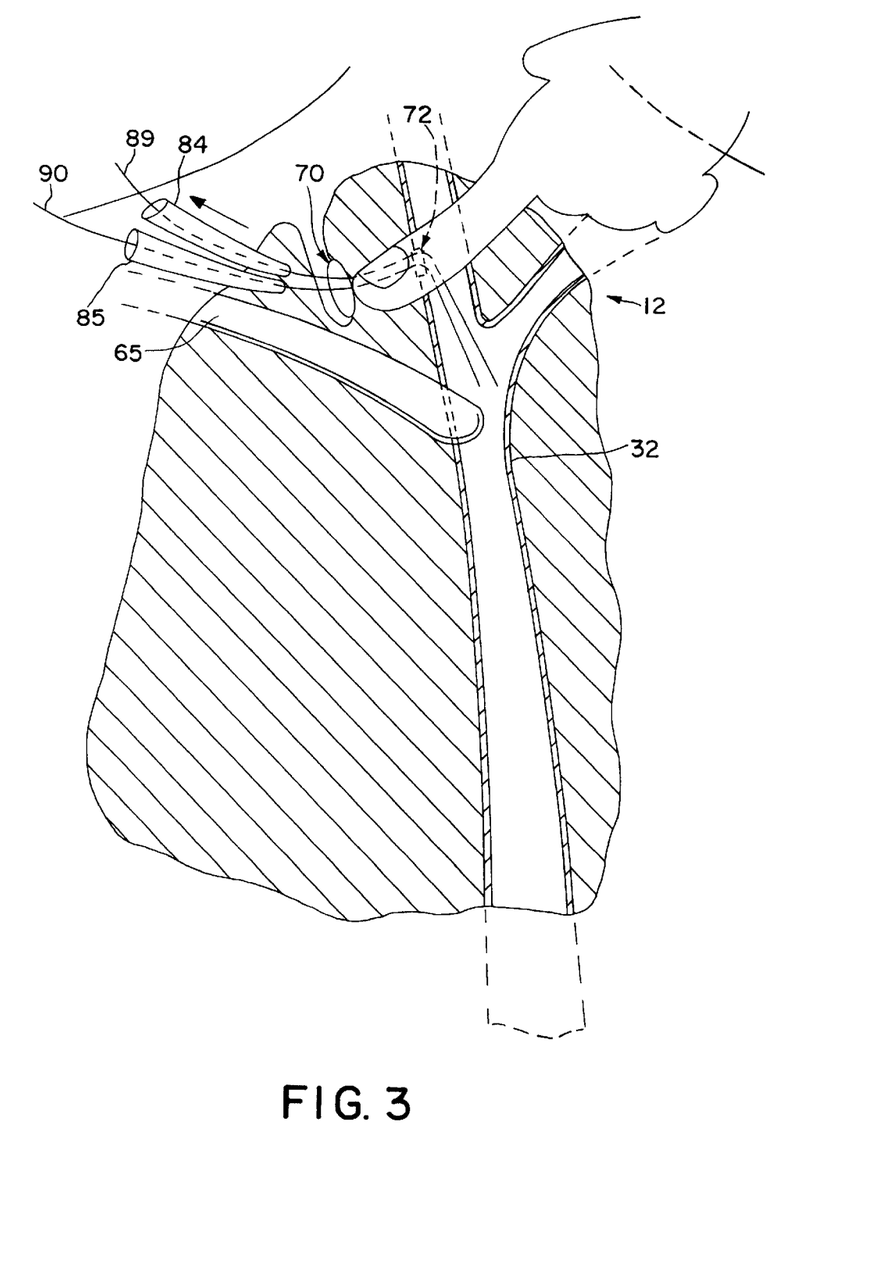
FIG. 3 is a partially broken-away diagrammatic view of the first and second dilators depicted in FIG. 2 being removed from the area to be catheterized while finger pressure is applied across the access site and the insertion site.
Figure 4:
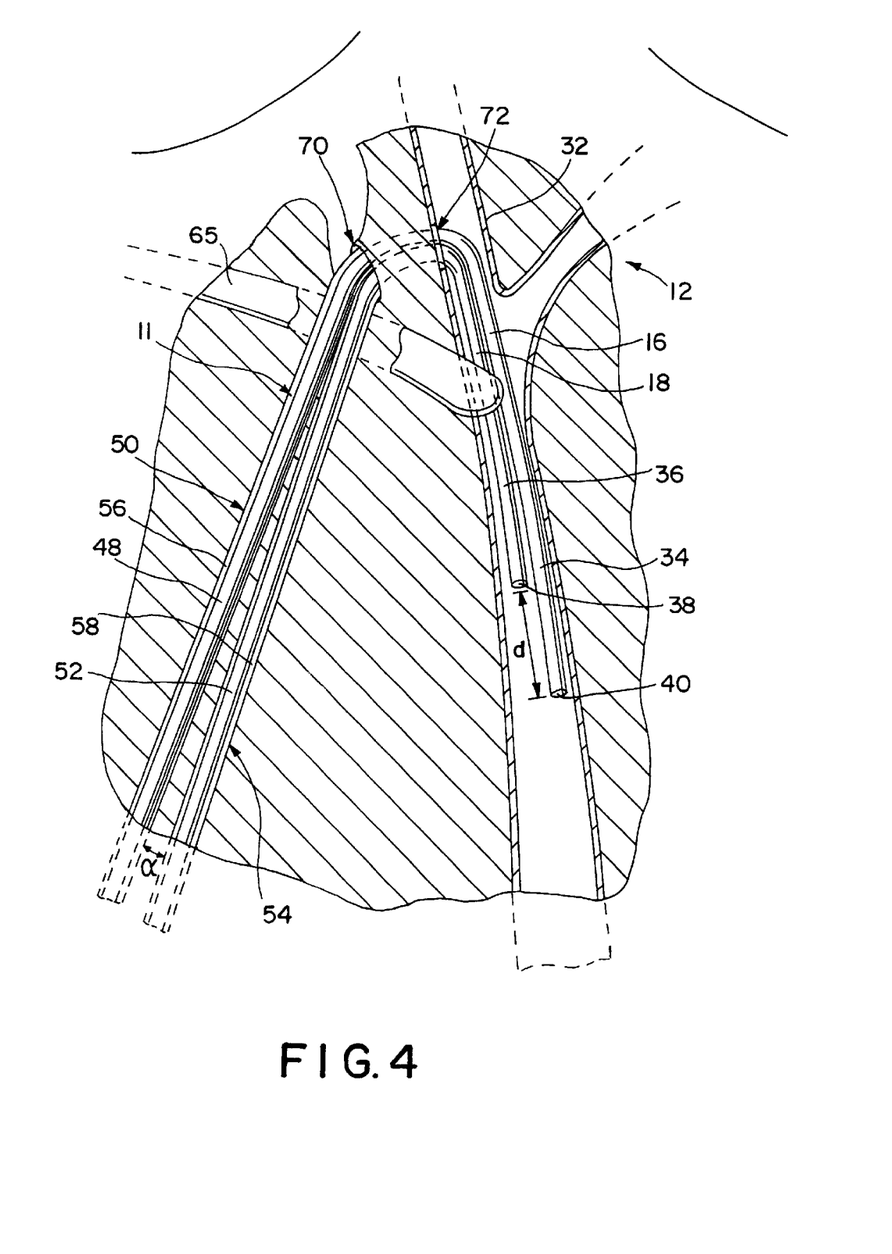
FIG. 4 is a partially broken-away diagrammatic view of a double catheter assembly after insertion into the internal jugular vein in accordance with an one embodiment of the present invention.

Referring now to the drawings in detail, there is shown in FIGS. 1 through 7, preferred embodiments of the insertion method of the invention, a self-retaining double catheter assembly, generally indicated as 10, and an alternative double catheter assembly, generally indicated as 11. The preferred catheter assembly 10 is the SchonCath® which is described in U.S. Pat. No. 5,718,692, and catheter assembly 11 is a Tesio catheter. However, the invention is not limited to inserting the catheters described herein, but rather the method of the invention can be performed using substantially any known multiple catheter assembly As shown in FIG. 4, once a catheter assembly 11 is properly inserted in an area to be catheterized 12, the assembly 11 is secured by subcutaneous tuneling. As shown in FIG. 4, the assembly 11, a Tesio catheter assembly, includes a first catheter 16 and a second catheter 18. In the catheter assembly 11, the first and second catheters 16, 18 are unattached to each other along their entire length (i.e. independently movable with respect to each other along their entire length). Such an assembly is contemplated as within the present invention as an alternative assembly adaptable for other related applications. In addition, a catheter assembly 11 may further comprise at least one anchoring device, such as a fabric tissue ingrowth cuff (not shown) formed of Dacron® polyester or the like. By way of example, a fabric cuff can be affixed to the exterior surface 20 of the proximal portions 48, 52 of the catheters 16, 18 within the assembly 11, and may be used to secure the assembly in the area to be catheterized 12 or to prevent infection. The method of the invention may further be used to insert a catheter assembly 11 comprising more than two single lumen catheters, more than one multi-lumen catheter, or a combination thereof. Where the present invention is described below using the assembly 10 embodiment, it is understood to include, unless otherwise stated, the use of alternative assembly 11 comprising at least two single lumen catheters 16, 18, as shown in FIG. 4.

Figure 5:
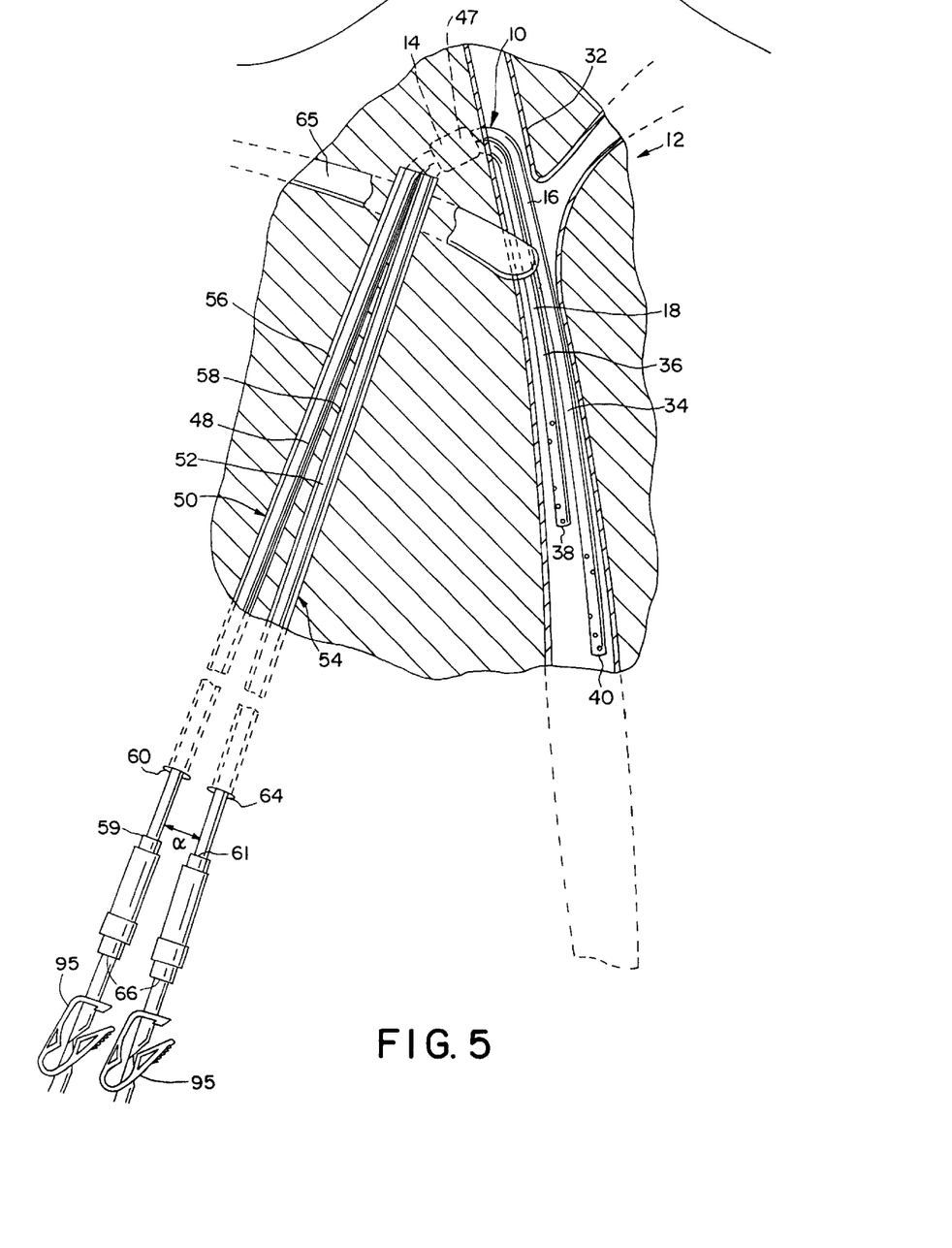
FIG. 5 is a partially broken-away diagrammatic view of a preferred double catheter assembly after insertion into the internal jugular vein in accordance with a preferred embodiment of the present invention.

As shown in FIG. 5, once a catheter assembly 10 is properly inserted in an area to be catheterized 12, the assembly 10 is self-retaining in that it is secured by the retaining sleeve generally indicated as 14. As shown in FIGS. 5, the assembly 10, which has been previously described (Schon et al. U.S. Pat. No. 5,718,692, incorporated herein by reference) includes a first catheter 16, a second catheter 18, and the retaining sleeve 14. The catheter assembly 10 comprises the first and second catheters 16, 18 attached to each other by a retaining sleeve 14, best shown in FIGS. 5, 6, and 7, which either fits around one or both of the catheters 16, 18, and either allows one or both of the catheters 16, 18 to be adjusted relative to the other catheter or within an area to be catheterized, or more preferably, is permanently linked to one or both of the catheters 16, 18.

It will be understood from this disclosure, that additional catheters (not shown), including multiple lumen catheters, which may have distal portions inserted into the area to be catheterized in a manner as shown in FIG. 5, could also be positioned within the retaining sleeve 14 such that proximal portions of such catheters are drawn out of the body through two or more subcutaneous areas and the retaining sleeve 14 would function to secure all of the catheters in position. Such an assembly is contemplated as within the present invention as an alternative self-retaining assembly adaptable for other related applications. However, for clarity and convenience, the present invention will be described below in the preferred assembly which includes a double catheter assembly having two single lumen catheters 16, 18 and a retaining sleeve 14 as shown in FIG. 5.

The catheter assemblies 10 and 11 can be adapted for use in various applications in which bodily fluids, medicaments or other solutions are introduced and removed from the body such as perfusion, infusion, plasmapheresis, hemodialysis, chemotherapy, and the like. For the purposes of describing the preferred embodiment of the present invention, the device will be described with respect to the preferred application of hemodialysis. However, it should be understood by one skilled in the art based on this disclosure, that the assemblies 10 and 11 can be configured and adapted, by increasing or decreasing the catheter size, catheter number, or both, and with respect to assembly 10, by positioning the retaining sleeve, such that the assembly 10 can be beneficially used for other medical applications in which fluids are introduced, removed, or introduced and removed from the body.

The first catheter 16, the second catheter 18 and the retaining sleeve 14 are all preferably made of a biocompatible plastic or elastomer, more preferably from a biocompatible elastomer. Suitable biocompatible plastics include materials such as, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene and other similar compounds known to those skilled in the art. It should be understood that these possible biocompatible polymers are included above for exemplary purposes and should not be construed as limiting. If a biocompatible polymeric material is used to form the catheters 16, 18 and the retaining sleeve 14, it is most preferred that the polymeric material includes a polyurethane or a polyolefin polymeric material.

Suitable, preferred, biocompatible elastomers for use in forming the catheters 16, 18 and the retaining sleeve 14 include biocompatible elastomers such as medical grade silicone rubbers, polyvinyl chloride elastomers, polyolefin homopolymeric and copolymeric elastomers, urethane-based elastomers, and natural rubber or other synthetic rubbers. Preferably, the catheters 16, 18 and the retaining sleeve 14 are made of the elastomeric material such that the catheters 16, 18 and retaining sleeve 14 are flexible, durable, soft, and easily conformable to the shape of the area to be catheterized 12 and/or the subcutaneous areas as described below. It is more preferred that the catheters 16, 18 and retaining sleeve 14, if used for hemodialysis applications particularly, be formed of a silicone elastomer which is preferably capable of withstanding sterilization by autoclave and preferably has a hardness of at least about 80-A on a Shore durometer scale. While it is preferred to have a higher Shore durometer hardness if a biocompatible elastomer is used, particularly for hemodialysis, it is also possible to make a device from an elastomer having a lower Shore durometer hardness without departing from the spirit of the invention. It will be understood, based on this disclosure, that the catheters 16, 18 may also be radiopaque depending on their intended use.

Figure 7:
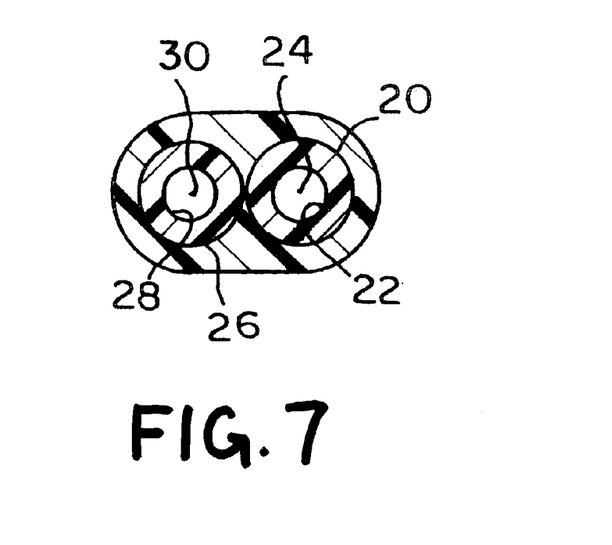
FIG. 7 is an enlarged cross-sectional view of the retaining sleeve shown in FIG. 6 taken along line 4—4.

As shown in FIG. 7, the first catheter 16 has an exterior surface 20 and an interior surface 22 defining a first lumen 24. The first lumen 24 extends longitudinally through the first catheter 16, preferably along the full length of the catheter 16. In a similar manner, the second catheter 18 has an exterior surface 26 and an interior surface 28 defining a second lumen 30. The second lumen 30 extends longitudinally through the second catheter 18, preferably along the full length of the catheter 18. The lumens 24, 30 preferably each have a generally circular cross section as viewed along a plane perpendicular to the longitudinal axis of each of the catheters 16, 18.

While the circular cross section is preferred in order to achieve efficient fluid flow in each lumen 24, 30, other configurations may be used without departing from the spirit of the present invention, such as for example, oval, elliptical, or kidney-bean shaped. While configurations such as semi-circular, rectangular, and the like may be used, they are not preferred as the sharper corners may increase turbulent flow within the lumens 24, 30.

In addition, while two lumens 24, 30 of equal cross-sectional area are preferred, the two lumens 24, 30 in the catheter assembly 10 may be of different cross-sectional areas (such as, for example, providing a smaller lumen for infusion of medication). Alternatively, two lumens 24, 30 of equal cross-sectional area may be provided along with an additional lumen (not shown) which may have the same or a different cross sectional area (such as, for example, a hemodialysis catheter having two lumens of equal cross-sectional area for removal and return of blood and a third lumen of a smaller circular cross-section for infusion of medication).

As illustrated in FIGS. 4 and 5, a double catheter assembly 10 or 11 may comprise a first catheter 16 which is presized to have a first longitudinal length and a second catheter 18 which is presized to have a second longitudinal length shorter than the first longitudinal length by the distance d (i.e., the first catheter 16 is longer than the second catheter 18 by the distance d). Alternatively, the first and second catheters 16 and 18 are identical in longitudinal measure. One or both of the first and second catheters 16, 18 may be provided with markings for use in adjusting the longitudinal distance between the proximal portions of the catheters 16, 18.

The catheters 16, 18 can be used for the introduction and removal of fluids from an area to be catheterized, such as the area 12 as shown in FIGS. 4 and 5. In FIGS. 4 and 5, the area to be catheterized includes the internal jugular vein 32. Other areas in which the catheter assemblies 10, 11 may be used include, for example, other blood vessels, including the femoral and subclavian veins, any abscess cavity, post-operative cavity, the peritoneal cavity, and other areas of the body including intra-abdominal, sub-diaphragmatic and sub-hepatic areas. It should be understood by one of ordinary skill in the art from this disclosure that these areas are exemplary, and that the catheter assembly 10 may be used to remove or introduce fluids in various areas to be catheterized. The preferred embodiment of the invention as shown, is preferably useful for intake, or removal, of blood to be purified from a blood vessel, such as the internal jugular vein 32, and introduction of purified blood into the same vessel as shown in FIG. 5. The blood can be purified by any suitable hemodialysis apparatus (not shown). The catheters 16, 18 may also be used to introduce medication or other fluids such as glucose or saline solutions into the body.

The catheters 16, 18 each include a distal portion 34, 36 respectively as shown in FIGS. 4 and 5. The distal portions 34, 36 are configured to be placed in, or preferably inserted into, the area to be catheterized 12. For example, as shown in FIG. 5, the distal portions 34, 36 of the catheters 16, 18 are configured to have a suitable length and width to be useful for insertion into the internal jugular vein 32. If used for hemodialysis applications particularly, it is preferred that the distal end 38 of the second catheter 18 is proximally and longitudinally spaced from the distal end 40 of the first catheter 16 a sufficient distance d (indicated in FIG. 4) which substantially prevents recirculation of the purified blood and blood to be purified. The distance d, is preferably about 3 centimeters, however, it should be understood by one of ordinary skill in the art based on this disclosure, that the distance d could be varied for different applications of either catheter assembly 10 or 11.

Figure 6:
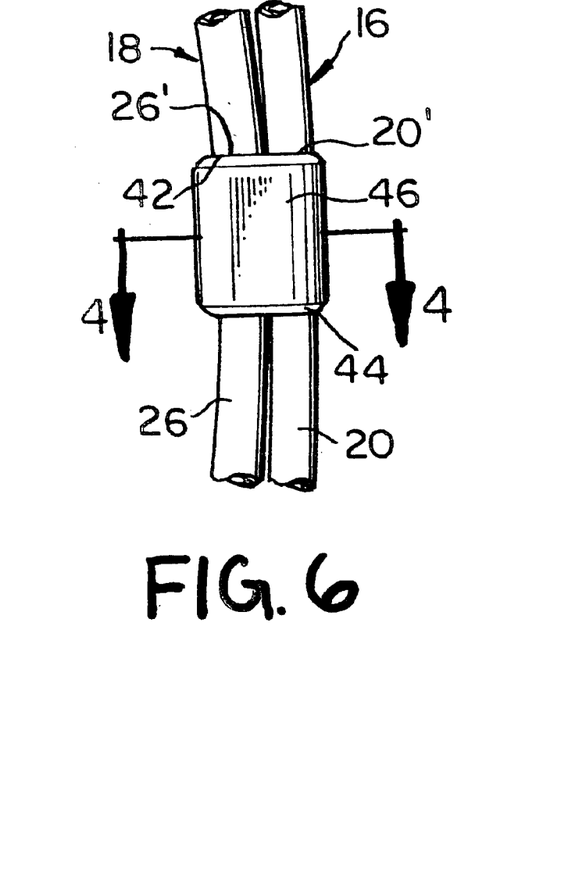
FIG. 6 is an enlarged view of the retaining sleeve in the catheter assembly shown in FIG. 5.

A retaining sleeve 14, best shown in FIGS. 6 and 7, is located on the catheter assembly 10 proximal to the distal ends 40, 38 of the first and second catheters 16, 18. The retaining sleeve is positioned around a portion 20' of the exterior surface of the first catheter 16 and a portion 26' of the exterior surface 26 of the second catheter 18. The portions 20', 26' of the exterior surfaces 20, 26 of the first and second catheters 16, 18 within the retaining sleeve 14 are preferably juxtaposed to one another. While the portions 20', 26' within the sleeve 14 may be spaced from one another, it is preferred that they are close together, preferably touching to avoid entry of bodily fluids, such as blood, into the retaining sleeve 14. The top and bottom edges 42, 44 of the retaining sleeve 14 may be beveled, extending from the external surface 46 of the retaining sleeve 14 toward the exterior surfaces 20, 26 of the catheters 16, 18. Beveled edges 42, 44, as shown in phantom in FIG. 5, may help to prevent fluid from entering into the retaining sleeve 14. Alternatively, the edges 42, 44 may be at a substantially right angle to the exterior surface 46 of the retaining sleeve 14.

Regardless of the configuration of the edges 42 and 44 of the retaining sleeve 14, it is important that the retaining sleeve 14 be made sufficiently wide to prevent the retaining sleeve 14 from passing into the vein 32 or other area to be catheterized 12, such that the retaining sleeve remains outside the area to be catheterized 12 after insertion. As such, the retaining sleeve 14 is preferably sufficiently wide as to be larger than the insertion site 72 (i.e. the opening into the area to be catheterized 12 made through the recessed area 47).

In hemodialysis applications, wherein the retaining sleeve 14 of the catheter assembly 10 is permanently linked to an exterior portion of one or more of the catheters 16, 18, the assembly 10 is preferably introduced by means of a tear-away sheath assembly as described below. Preferably, the retaining sleeve 14 is wider than the tear-away sheath assembly such that it does not pass into the sheath when the distal portions 34, 36 of the catheters 16, 18, are inserted in the vein 32.

The catheter assembly 10 in which the retaining sleeve 14 is adjustable can be introduced by means of substantially any appropriately sized introducer sheath assembly known in the art. The introducer can be a tear-away assembly, or alternatively, the catheters 16, 18 can be inserted independently using a standard introducer. In this embodiment, a physician, or other medical personnel, can position the retaining sleeve 14 on the catheters 16, 18 prior to or after insertion of the distal ends 40, 38 of the catheters 16, 18 into the vein 32.

Figure 1:
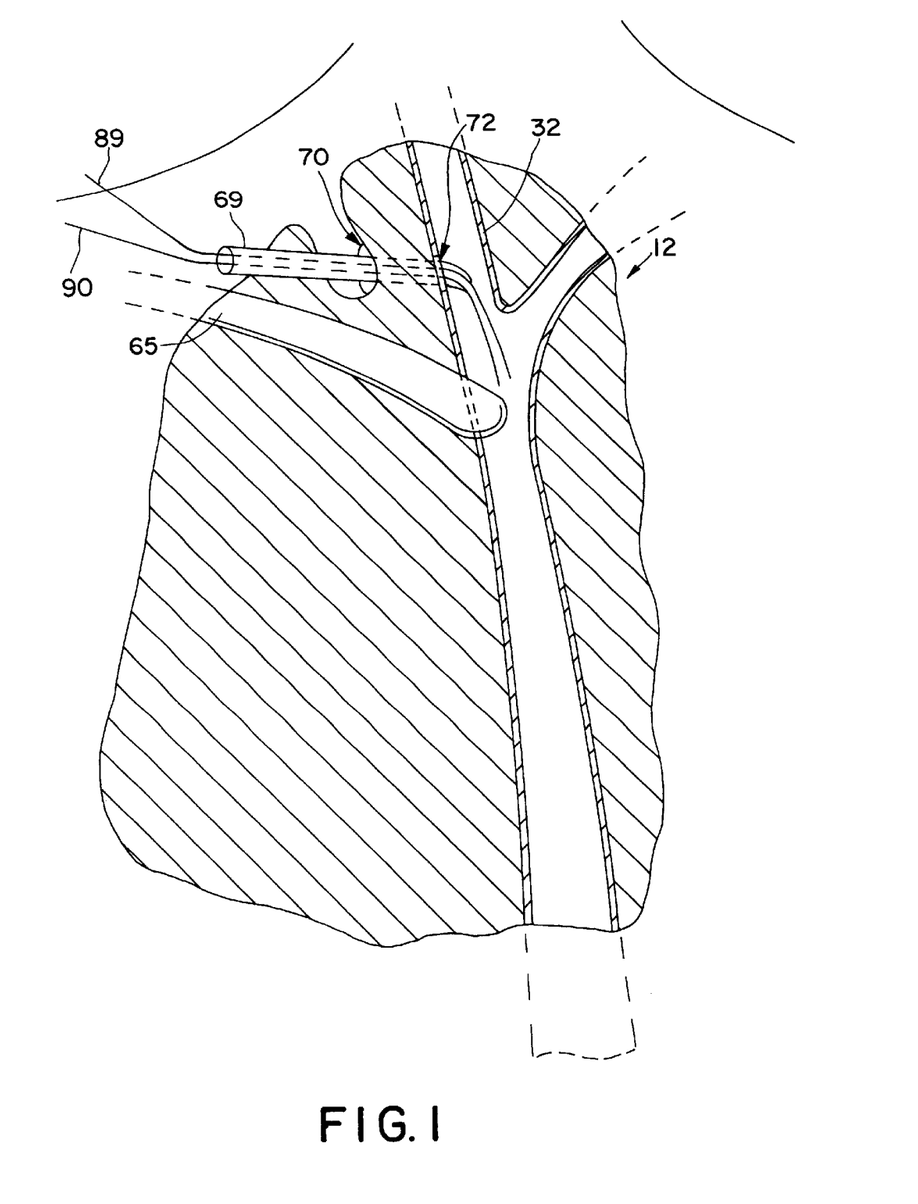
FIG. 1 is a partially broken-away diagrammatic view of an introducer sheath positioned through the access site and the insertion site, partially extending into the internal jugular vein, in accordance with an embodiment of the present invention.

In a preferred embodiment of catheterization shown in FIG. 1, wherein the area to be catheterized is the internal jugular vein, the introducer sheath 69 has a transverse width of from about 6 French to at least about 20 French. The shape and size of the sheath may vary to accommodate the shape of a catheter or catheters placed together. In the case of the SchonCath®, the sheath is elliptical. The sheath must also be large enough to permit passage of the catheters when placed together through the sheath. However, the sheath size may vary for different sized catheters and applications of use. Transverse width as it relates to the introducer sheath 69, shown in FIG. 1, is a measurement of the interior cross-sectional width, that is, the diameter of the circular, interior cavity formed by the introducer sheath 69.

The retaining sleeve 14 is preferably sized to fit around the first and second catheters 16, 18 when the catheters 16, 18 are arranged in a preferably juxtaposed relationship. The retaining sleeve 14, is preferably longitudinally sized to fit within the recessed area 47, shown in phantom in FIG. 2, lying proximal to the insertion site 72 into the vein 32, below the access site 70 into the body of the patient, and distal to the caudally disposed subcutaneous areas for securement. If the catheter assembly 10 is used for hemodialysis and the area to be catheterized 12 is the internal jugular vein 32, a recessed area 47 will be made in the vicinity of the clavicle 65, as shown, for example, in FIG. 5. The exact location of the recessed area 47 can be slightly varied by the physician, but should be at least large enough to substantially contain the retaining sleeve 14. The recessed area 47 and the retaining sleeve 14 should be sized to fit in a location outside the vein 32, beneath the access site 70 and proximal to the insertion site 72, such that the retaining sleeve 14 is embedded in subcutaneous tissue as shown, for example, in FIG. 5.

The retaining sleeve 14, in hemodialysis applications, is preferably about 1 centimeter in length as measured along a longitudinal axis of the retaining sleeve 14. The inner width of the sleeve 14 is determined in accordance with the outer diameters of the catheters 16, 18 positioned within the sleeve 14 such that an appropriate fit is provided between the sleeve 14 and the catheters 16, 18. The exterior width of the sleeve 14 is preferably determined such that the sleeve 14 is configured to be sufficiently wide or large such that it does not pass or otherwise enter into the area to be catheterized 12 through an opening into the area to be catheterized 12 made through the recessed area 47, when the catheter assembly 10 is being positioned in the area to be catheterized 12.

In the alternative catheter assembly 11, shown in FIG. 4, in which the catheters 16 and 18 are independent and unattached, the recessed area 47, which is created to contain the retaining sleeve 14 of the preferred embodiment, is unnecessary. In this embodiment, adjustment of the first and second catheters, each of which is independently adjustable, may be performed by substantially any means which results in an appropriate longitudinal separation distance d between the distal portions 30, 34 of the two catheters 16, 18. The scope of the invention also includes performing the method described herein with single lumen catheters marked externally in substantially any manner that provides a means to adjust the relative longitudinal spacing between the distal portions 30, 34 of the two catheters 16, 18.

The first catheter 16 has a first proximal portion 48 configured to be placed within a first subcutaneous area 50. In a similar manner, the second catheter 18 has a second proximal portion 52 configured to be placed within a second subcutaneous area 54. The first and second subcutaneous areas 50, 54 preferably include first and second subcutaneous tunnels 56, 58, respectively. The subcutaneous tunnels are preferably formed using a tunneling device (not shown) such as a stainless steel trocar which, for example, attaches to a first proximal end 59 of the first proximal portion 48 of the first catheter 16 and pulls the proximal portion 48 beneath the skin while forming a subcutaneous tunnel 56. The end 59 of the proximal portion 48 is drawn by the device percutaneously out through an opening 60 in the patient's skin preferably about 6 to about 8 inches (about 15.2 to above 20.3 cm) caudal to the recessed area 47 of the catheter assembly 10 such that the first subcutaneous tunnel 56 extends from proximate to the recessed area 47 caudally through the subcutaneous area 50 to the opening 60. The end 59 of the catheter 16, when inserted extends outside the opening 60.

The second proximal end 61 of the second proximal portion 52 of the second catheter 18 is drawn by the device out through an opening 64 in the patient's skin preferably about 6 to 8 inches caudal to the recessed area 47 of the catheter assembly 10 such that the second subcutaneous tunnel 58 extends from proximate to the recessed area 47 caudally through the subcutaneous area 54 to the opening 64. When inserted, the end 61 extends outside the opening 64. The opening 60 and the opening 64 are spaced a distance from one another such that an acute angle α is formed between a line extending from the retaining sleeve 14 to the opening 60 and a line extending from the retaining sleeve 14 to the opening 64. The angle α between the tunnels 56, 58 may be varied from a small angle in which the tunnels 56, 58 are close to parallel to each other to a larger angle in which the tunnels 56, 58 and their openings 60, 64 are further apart without departing from the scope of the invention. It is preferred that the angle α be small enough that flow through the lumens 24, 30 is unobstructed. The angle is preferably from about 5° to about 120°, more preferably from about 5° to about 20°, and most preferably from about 10° to about 15°. In the case of a standard Tesio catheter such as assembly 11, the angle α is unnecessary, since assembly 11 is not self retaining.

In alternative embodiments, such as those in which the method is used for an acute catheterization, the catheter assembly is secured by affixing the assembly externally to the body of the patient. For example, a Tesio catheter assembly (U.S. Pat. No. 5,776,111), which may be inserted by the present method and which is designed specifically for acute catheterizations, is not secured by subcutaneous tunneling as shown in FIG. 4, but rather is secured externally to the patient's skin either by suturing or applying tape.

Connectors 66 may be attached to the proximal ends 59, 61 of the catheters 16, 18 such that the catheters 16, 18 may be attached to other devices such as, for example, a hemodialysis apparatus or an injection system. Other devices will be apparent to those of ordinary skill in the art based on this disclosure. Examples of suitable connectors 66 include quick connect fittings, ferrule connectors, threadable connectors, and the like. Locks or clamps 95, such as, for example, conventional luer locks, may also be provided to the proximal portions 48, 52 of the catheters 16, 18 for regulation or interruption of flow of fluid through the lumens 24, 30.

In the method of the present invention, a vein 32 is accessed using, for example, the standard Seldinger technique at an access site 70, appropriately proximate to the insertion site 72 which is near or proximate the area to be catheterized 12. A marked guide wire is used to determine the appropriate catheter size to be used in the procedure. It will be understood based on this disclosure that the parameters involved in making such a determination are known to those skilled in the art. If the catheter assembly 10 is used for hemodialysis and the area to be catheterized 12 is the internal jugular vein 32, the access site 70 is made in the clavicular triangle region, as shown for example, in FIGS. 1 through 5. The exact location of the insertion site 72 can be varied by the physician.

In accordance with the Seldinger technique, a narrow needle would normally be inserted through the access site 70 and into the vein 32 at the insertion site 72. A guide wire would then be passed through the needle and the needle would be removed. The next step would be to advance a catheter over the guide wire. However, in the preferred embodiment of the present method, in which the vein 32 is the internal jugular vein, an introducer sheath is inserted through the access site 70 and the insertion site 72, and partially into the vein 32, as shown in FIG. 1. The diameter of the introducer sheath may vary, but in this preferred embodiment, the introducer sheath is from about 6 French to about 8 French in diameter. The diameter is measured at the widest transverse section of the introducer sheath, 69.

Following placement of the introducer sheath 69, at least two guide wires 89 and 90, which can have a range of longitudinal measures from 100 centimeters to greater than 200 centimeters, and preferably, from 100 centimeters to 120 centimeters, are inserted through the sheath and into the accessed vein 32, as shown in FIG. 1. The sheath is removed, and the guide wires remain, extending distally from the access site 70 and proximally from the insertion site 72 into the vein 32.

Following insertion of the guide wires into the vein 32, an incision measuring from about 1 centimeter to about 1.5 centimeters longitudinally, is made at the access site 70, and a recessed area 47 is formed by excision of subcutaneous tissue which is proximal to the insertion site 72, and which is sufficient in its dimensions to contain the retaining sleeve 14 of the double catheter assembly 10 described above. For embodiments of the method which employ the catheter assembly 11, shown in FIG. 4, the recessed area 47 is not formed, since the assembly 11 lacks a retaining sleeve to place in the recessed area 47.

Once the recessed area 47 is formed, a dilator 84, 85 is introduced around each guide wire and inserted partially into the vein 32, as shown in FIG. 2 (not drawn to scale). Proper dilation of the vessel is critical in performing the method of the invention. It is preferred that once placed partially into the vein 32, each dilator 84, 85 is maneuvered using a vigorous and circumferential motion. By vigorous and circumferential motion is meant that after the distal portion of each dilator is partially extended into the vein 32 as shown in FIG. 2, the proximal portion of each dilator 84, 85 is grasped, and the dilator is maneuvered in a circular motion, contacting the wall of the vein 32 at the insertion site 72, in order to enlarge the insertion site 72. It is well within the ability of a skilled artisan to identify a motion which is sufficiently vigorous and circumferential with respect to the insertion site 72, given that the objective of performing the motion is to enlarge the insertion site 72 in preparation for inserting the catheters 16, 18.

The selection of a dilator for a given catheterization procedure is also important. The dilators for a catheter procedure are selected such that the sum of the diameters of the first and second dilators, each measured at its widest transverse section, is at least 3 French units greater than the sum of the diameters of the first and second catheter lumens 24, 30 to be inserted, also measured at the widest transverse section of each catheter lumen 24, 30. By way of example, if the sum of the diameters of two single lumen catheters placed side-by-side is 18 French, then the sum of the diameters of the dilators which should be used in the insertion method of the invention is 22 French (i.e. each dilator device is an 11 French dilator).

In prior insertion techniques, the next step would be the removal of the guide wires and the insertion of a sheath over a dilator, both inserted over a wire. The diameter of the sheath would be at least equal to the sum of the 1st and 2nd catheter lumens 24, 30 to be inserted side by side. The dilator must then be removed. However, the removal of dilators in these procedures can result in increased bleeding and clotting at the access and insertion sites, and can promote the formation of an air embolism. Additionally, in difficult insertion procedures such as insertion of a double catheter assembly into the left internal jugular vein, a second guide wire is needed so that both lumens are inserted over guide wires to prevent the catheter curling or bending as it passes from the internal jugular vein at a sharp angle into the left innominate (brachio-cephalic) vein and then makes a second sharp turn to drop down into the superior vena cava. Since the second wire can only be passed through the sheath after the occluding dilator is removed, the sheath is open to air during this prolonged period. Thus very significant blood loss and a high potential for air embolism may be incurred during the manipulation of the second wire even before the attempted threading of the catheter assembly over the two wires and into the superior vena cava.

In the present invention, the insertion of the dilator-sheath assembly is eliminated. After removal of the dilators the sheath assembly is not inserted and the flow of air, blood, or both to the area to be catheterized 12 is blocked, particularly across the access site 70 and the insertion site 72. The blood and air flow can be blocked either before, during, or after removing the dilators from the area to be catheterized 12. However, it is preferred that the flow of blood and air to the area to be catheterized 12 is blocked during the removal of the first and second dilators from the area to be catheterized 12. Subsantially any suitable method of blocking the flow of blood and air to an incision, which decreases bleeding and discourages the formation of air embolisms at the access site 70 and at the insertion site 72, may be used in the present method. One preferred method of blocking blood and air flow, illustrated in FIG. 3, is to apply pressure using at least one finger across the access site 70 and the 30 insertion site 72 by finger or other mechanical compression.

In accordance with the method of the present invention, the distal portion of each catheter in the double catheter assembly 10 is threaded onto a remaining guide wire and inserted through the access site 70 and insertion site 72, and into the vein 32. The distal portion of the catheters are inserted until they are properly positioned within the area 12, as shown in FIGS. 4 and 5. Each of the catheters 16, 18 may freely and independently move within the area to be catheterized 12.

Once the multiple catheter assembly 10 is inserted, and the incision is closed, the assembly 10 is secured. As generally described above, FIG. 5 shows a securing method which is useful in chronic procedures using a self-retaining assembly such as assembly 10. Accordingly, the proximal portions 48, 52 of the catheters 16, 18 are tunneled through the subcutaneous areas 50, 54 as generally described above. The incision site 47 and any tunneling incisions are closed and a dressing is preferably applied.

In alternative embodiments, a catheter assembly 10, 11 may be stabilized, protected from infection, or both using a fabric tissue ingrowth cuff formed of Dacron® polyester or the like (not shown). The fabric cuff can be affixed to the exterior surfaces 20 of the proximal portions 48, 52 of the catheters 16, 18 within an assembly 10, 11, and may be positioned such that subcutaneous tissue, which is proximate to the area to be catheterized 12, infiltrates and grows into the fabric, thereby anchoring the assembly in place. As such anchoring devices and methods of using them are known in the medical art, it is considered well within the ability of one skilled in the art to identify catheterization procedures for which an assembly comprising a fabric cuff is useful, and use the cuff in securing the assembly and preventing infection.

As applied to catheter assembly 10, when the proximal portions 48, 52 are positioned in subcutaneous areas 50, 54, preferably in the subcutaneous tunnels 56, 58, the retaining sleeve 14 is embedded in subcutaneous tissue (i.e. the recessed area 47) and positioned outside the area to be catheterized 12 and distal to the first and second subcutaneous areas 50, 54. By positioning the retaining sleeve 14 in this manner, a generally Y-shaped configuration is achieved having the angle α as previously described. The retaining sleeve 14 thereby secures the assembly 10 in place, and the assembly 10 cannot be pulled from the area of catheterization 12 or subcutaneous areas 50, 54 due to the location of the retaining sleeve 14 in the recessed area 47, between the area to be catheterized 12 and the subcutaneous areas 50, 54. As shown in FIG. 5, the retaining sleeve 14 (depicted in phantom lines) is positioned outside the vein 32 and distal to the first and second subcutaneous tunnels 56, 58, in the recessed area 47.

In the disclosed embodiment, all incisions are closed before the catheterization procedure begins. If necessary, catheterization may be performed with an open incision, although the preferred technique is to close all incisions before performing catheterization.

The method of catheter insertion provided by present invention offers significant advantages over prior art methods of inserting double catheter assemblies, including the ability to insert two catheters with a single insertion procedure that is significantly safer, by reducing bleeding, undesirable clotting, and the potential for developing an air embolism during the procedure. Double catheter assemblies such as the Tesio catheter which are not attached and are usually placed separately require a second puncture of a central vessel such a the internal jugular or subclavian veins. This may result in twice the potential for inadvertent puncture of the internal jugular artery or subclavian artery and associated hemorrhagic complications or of a lung and resultant pneumotherax. The current method allows effective insertion of such an assembly by means of a single vessel puncture and thus theoretically halves the risk of such complications.

In another aspect, the invention includes a kit which is useful in performing a method of the invention. A "kit" is any package, container, or other components which are promoted, distributed, of sold as a unit for performing a method of the invention, or as separate components with the intention that the components be used cooperatively by the recipient to perform a method of the invention. By way of example, a kit of the invention can comprise one or more components useful for inserting a self-retaining or non-self-retaining double catheter assembly into the internal jugular vein of a human patient for the purpose of hemodialysis according to a method described herein. Although an exemplary kit is now described, the contents of other useful kits will be apparent to the skilled artisan in light of the present disclosure.

The present invention includes a kit comprising at least one of each of a multiple catheter assembly, an introducer sheath, and a dilator, at least two guide wires, and an instructional material which outlines, illustrates, or describes a method included in the present invention. The multiple catheter assembly can be, for example, a Tesio catheter assembly, a SchonCath assembly, or other multiple catheter assembly requiring a two wire insertion procedure, and may be included in a kit which also comprises an introducer sheath, two dilators, two guide wires and an instructional material. A kit can further comprise one or more replacement catheters, and can optionally include one or more of a disposable syringe, a tunneling device, a connector, and a clamp.

Each of the components of a kit described herein can be promoted, distributed, or sold either as a unit or as separate components to be used cooperatively. By way of example, the instructional material can be affixed to a container which contains one or more of the catheter insertion components described herein, or the instructional material can be shipped together with one or more containers which individually contain one or more catheter insertion components. By way of alternative example, the instructional material may be shipped separately from the catheter insertion components with the intention that the instructional material and the catheter insertion components be used cooperatively by the recipient.

The instructional material included in a kit of the invention can be a publication, a recording, a diagram, or any other medium of expression which can be used to communicate one or more of the steps of a catheter insertion method included in the present invention. The instructional material can also include any medium of expression which is used to communicate the parameters within which to perform the steps of a method of the invention, and troubleshooting indications and precautions as would be obvious to one skilled in the art after reading the present disclosure. The instructional material of a kit included in the invention may comprise a plurality of materials which can be provided with one or more components of the kit. By way of example, an instructional material can comprise a document which lists the steps of the present catheterization method, and which is provided with an introducer sheath of the kit, and a videographic material which illustrates the method as performed on the internal jugular vein of a human patient, and which is provided with a double catheter assembly of the kit.

The disclosure of every patent, patent application, and publication cited herein is hereby incorporated herein by reference in its entirety.

While the present invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A method for inserting a multiple catheter assembly into an area of a body to be catheterized, the assembly comprising a first and a second catheter, the method comprising the steps of:
   a. accessing an area to be catheterized and creating an access site;
   b. inserting an introducer sheath into the area to be catheterized;
   c. inserting a first guide wire and a second guide wire into the introducer sheath;
   d. at least partially inserting a first dilator over the first guide wire and a second dilator over the second guide wire into the area to be catheterized;
   e. removing the first dilator and the second dilator and blocking the flow of one or more of blood and air into and out of the area to be catheterized;
   f. passing the distal portion of the first catheter over the first guide wire and passing the distal portion of the second catheter over the second guide wire; and
   g. inserting each of the first and second catheters in juxtaposed relation into the area to be catheterized.

2. The method of claim 1, wherein the multiple catheter assembly further comprises a retaining sleeve, and wherein the method further comprises making an incision at the access site and creating a recessed area directly under the incision, which recessed area is sized to contain the retaining sleeve.

3. The method of claim 2, wherein each of the first dilator and the second dilator has a diameter of 11 French, which diameter is measured in the transverse direction.

4. The method of claim 2, wherein the incision made at the access site is from about 1 centimeter in length to about 1.5 centimeters in length.

5. The method of claim 2, further comprising closing the incision made at the access site.

6. The method of claim 1 further comprising subcutaneously securing a proximal portion of the first catheter and a proximal portion of the second catheter.

7. The method of claim 6, the method further comprising forming at least one subcutaneous tunnel and threading the proximal portion of at least one of the first and second catheters therethrough.

8. The method of claim 1, wherein the area to be catheterized is a blood vessel.

9. The method of claim 8, wherein the area to be catheterized is an internal jugular vein of a human, which vein is proximal to the right atrium of the heart of the human, and wherein the distal portion of the first catheter is closer to the heart than the distal portion of the second catheter.

10. The method of claim 1, further comprising the step of attaching a removable connector having a fluid passageway to the proximal portion of each of the first and the second catheters.

11. The method of claim 10, wherein the removable connectors each include an extension tube having a clamp that controls fluid flow through the connector.

12. The method of claim 1, wherein each of the two wires is from about 100 centimeters in length to about 120 centimeters in length.

13. The method of claim 1, wherein the sum of the diameters of the first and second dilators is at least 3 French greater than the sum of the diameters of the first and second catheters.

14. The method of claim 1, wherein step (d) further comprises maneuvering each of the first and second dilators vigorously and circumferentially within the area to be catheterized.

15. The method of claim 1, wherein the proximal portions of the first and second catheters each include at least one subcutaneous securement device.

16. The method according to claim 1, wherein the first catheter is longer than the second catheter, as measured longitudinally.

17. The method of claim 1 further comprising closing the incision made at the access site.

18. A method for inserting a multiple catheter assembly into an area of a body to be catheterized, the method comprising the steps of:
- a. accessing an area to be catheterized;
- b. inserting an introducer sheath into the area to be catheterized;
- c. inserting a first guide wire and a second guide wire into the area to be catheterized by passing the guide wires through the introducer sheath;
- d. inserting and then removing a first dilator and a second dilator into the area to be catheterized; and
- e. inserting a first catheter and a second catheter into the area to be catheterized by passing the first catheter over the first guide wire and the second catheter over the second guide wire and threading each into the area to be catheterized.

19. A method for inserting a multiple catheter assembly into an area of a body to be catheterized, the method comprising the steps of:
- a. accessing an area to be catheterized;
- b. inserting an introducer sheath into the area to be catheterized;
- c. inserting a first guide wire and a second guide wire into the area to be catheterized by passing the guide wires through the introducer sheath;
- d. removing the introducer sheath;
- e. inserting and then removing a first dilator and a second dilator into the area to be catheterized by passing the first dilator over the first guide wire and the second dilator over the second guide wire and threading each into the area to be catheterized; and
- f. inserting a first catheter and a second catheter into the area to be catheterized by passing the first catheter over the first guide wire and the second catheter over the second guide wire and threading each into the area to be catheterized.

* * * * *

UNITED STATES PATENT AND TRADEMARK OFFICE
CERTIFICATE OF CORRECTION

PATENT NO.     : 6,682,519 B1
DATED          : January 27, 2004
INVENTOR(S)    : Donald A. Schon It is certified that error appears in the above-identified patent and that said Letters Patent is hereby corrected as shown below:

<u>Title page,</u>
Item [75], please change the spelling of the inventor's address from "Pheonix" to
-- Phoenix --.

Signed and Sealed this

Thirtieth Day of March, 2004

JON W. DUDAS
*Acting Director of the United States Patent and Trademark Office*